(12) United States Patent
Benaskar et al.

(10) Patent No.: US 11,414,361 B2
(45) Date of Patent: Aug. 16, 2022

(54) SYSTEMS AND METHODS FOR CONVERTING N-BUTANE TO ISO-BUTANE

(71) Applicant: SABIC Global Technologies B.V., Bergen op Zoom (NL)

(72) Inventors: Faysal Benaskar, Jubail Industrial (SA); Sami Muteib Al-Mutairi, Jubail Industrial (SA); Massimiliano Comotti, Jubail Industrial (SA); Adel Saud Al-Shafai, Jubail Industrial (SA); Mohammad I. Al-Somali, Jubail Industrial (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 153 days.

(21) Appl. No.: 16/642,143

(22) PCT Filed: Aug. 22, 2018

(86) PCT No.: PCT/IB2018/056375
§ 371 (c)(1),
(2) Date: Feb. 26, 2020

(87) PCT Pub. No.: WO2019/043523
PCT Pub. Date: Mar. 7, 2019

(65) Prior Publication Data
US 2020/0354288 A1 Nov. 12, 2020

Related U.S. Application Data

(60) Provisional application No. 62/551,180, filed on Aug. 28, 2017.

(51) Int. Cl.
*C07C 5/27* (2006.01)
*C07C 9/12* (2006.01)
(Continued)

(52) U.S. Cl.
CPC ............ *C07C 5/2705* (2013.01); *B01J 8/0453* (2013.01); *B01J 8/0496* (2013.01); *B01J 2208/0053* (2013.01); *B01J 2208/00168* (2013.01)

(58) Field of Classification Search
CPC ......... B01J 8/00; B01J 8/02; B01J 8/04; B01J 8/0446; B01J 8/0449; B01J 8/0453;
(Continued)

(56) References Cited

U.S. PATENT DOCUMENTS

| | | | |
|---|---|---|---|
| 3,541,181 A | 11/1970 | Bercik et al. | 260/683.67 |
| 3,631,219 A | 12/1971 | Myers et al. | 260/683.2 |

(Continued)

FOREIGN PATENT DOCUMENTS

| | | |
|---|---|---|
| WO | WO1993011090 A1 | 6/1993 |
| WO | WO2004058572 A1 | 7/2004 |

OTHER PUBLICATIONS

ATIS-IL Isomerization Catalyst, Albemarle Corporation, 1 page, copy obtained Mar. 27, 2017.
(Continued)

*Primary Examiner* — Natasha E Young
(74) *Attorney, Agent, or Firm* — Norton Rose Fulbright US LLP

(57) ABSTRACT

Systems and methods for isomerizing n-butane to form isobutane are disclosed. A segmented reactor system is used to isomerize n-butane. The segmented reactor system comprises a segmented reactor that includes a first catalyst bed and a second catalyst bed separated by a first heat exchanger. The catalyst in the first catalyst bed does not contact the catalyst in the second catalyst bed. During the exothermic process of isomerizing n-butane, the first heat exchanger
(Continued)

extracts heat from an intermediate product flowing from the first catalyst bed to the second catalyst bed to improve the conversion rate of n-butane.

18 Claims, 2 Drawing Sheets

(51) Int. Cl.
*B01J 8/00* (2006.01)
*B01J 8/02* (2006.01)
*B01J 8/04* (2006.01)
*B01J 19/00* (2006.01)
*B01J 19/24* (2006.01)

(58) Field of Classification Search
CPC . B01J 8/0496; B01J 19/00; B01J 19/24; B01J 2208/00; B01J 2208/00008; B01J 2208/00017; B01J 2208/00106; B01J 2208/00168; B01J 2208/0053; B01J 2219/00; B01J 2219/24; C07C 5/00; C07C 5/22; C07C 5/27; C07C 5/2702; C07C 5/2705; C07C 5/2708; C07C 5/271; C07C 5/2716; C07C 5/2724; C07C 9/00; C07C 9/02; C07C 9/10; C07C 9/12
See application file for complete search history.

(56) References Cited

U.S. PATENT DOCUMENTS

| | | | |
|---|---|---|---|
| 4,621,062 A | 11/1986 | Stewart et al. | 436/55 |
| 5,082,989 A | 1/1992 | Johnson | 585/748 |
| 7,611,677 B2 | 11/2009 | Louret et al. | 422/145 |
| 8,228,534 B2* | 7/2012 | Azuma | G03G 15/80 |
| | | | 358/1.15 |
| 8,367,884 B2* | 2/2013 | Waycuilis | B01J 8/0457 |
| | | | 585/359 |
| 8,790,507 B2 | 7/2014 | Krishna et al. | 208/64 |
| 2009/0214403 A1 | 8/2009 | Yanokuchi et al. | |

OTHER PUBLICATIONS

Butamer Process, UOP LLC, 2 pages, copy obtained Mar. 27, 2017.
International Search Report and Written Opinion from PCT/IB2018/056375 dated Dec. 12, 2018, 9 pages.

* cited by examiner

SYSTEMS AND METHODS FOR CONVERTING N-BUTANE TO ISO-BUTANE

CROSS REFERENCE TO RELATED APPLICATIONS

This application is a national phase application under 35 U.S.C. § 371 of International Application No. PCT/IB2018/056375, published as WO 2019/043523, filed Aug. 22, 2018, which claims priority to U.S. Provisional Patent Application No. 62/551,180 filed Aug. 28, 2017. The entire contents of each of the above-referenced disclosures is specifically incorporated by reference herein without disclaimer.

FIELD OF INVENTION

The present invention generally relates to a chemical conversion process and related reactor design. More specifically, the present invention relates to systems and methods for isomerizing alkanes with segmented catalyst beds.

BACKGROUND OF THE INVENTION

Isobutane is used to produce methyl-tertiary-butyl ether (MTBE), which is a common octane booster for gasoline. Typically, isobutane is produced by isomerizing n-butane over bifunctional catalyst of platinum impregnated aluminum oxide or alumina. Because the catalytic process for n-butane isomerization occurs in vapor phase, the feed stream comprising primarily n-butane is normally heated until it is fully vaporized before contacting the catalyst. The n-butane isomerization reaction is exothermic. Thus, heat removal during the reaction is desired in order to achieve a high conversion rate of n-butane to isobutane.

To maintain the feed n-butane vaporized throughout the isomerization process and remove the reaction heat generated from the n-butane isomerization, conventional systems typically utilize two separate fixed bed reactors in series for isomerizing n-butane. Reaction heat is removed at the outlet of each of the reactors. However, it can be complicated to independently control the temperature at the inlet of each reactor due to ongoing changes of catalyst properties and reaction heat. A continuous adjustment for the temperature at the inlet of the reactors is generally conducted throughout the whole process. Therefore, several heat exchange trains are installed at the outlet of each of the reactors in order to accurately and independently control the temperature of each reactor while removing the heat generated by the isomerization reaction. Consequently, process control for these systems can be highly complex, and thereby the equipment costs and the operating costs for isomerizing n-butane using the conventional systems can be high. Improvements in the systems and methods for isomerizing n-butane are desired.

BRIEF SUMMARY OF THE INVENTION

A method has been discovered for isomerizing n-butane to form isobutane. By using a segmented reactor comprising a first catalyst bed and a second catalyst bed with a heat exchanger disposed therebetween, the reaction heat can be efficiently removed with improved process control and process optimization, which in turn can reduce equipment costs compared to conventional systems for butane isomerization.

Embodiments of the invention include a method of isomerizing n-butane to form isobutane. The method may include flowing a feed stream comprising n-butane to a reactor. The reactor may comprise a first catalyst bed, a second catalyst bed and a heat exchanger disposed therebetween. The first catalyst bed and the second catalyst bed may be separate so that catalyst in the first catalyst bed does not contact catalyst in the second catalyst bed. The method may further include isomerizing, in the first catalyst bed, at least some of the n-butane in the feed stream to form a first amount of isobutane. The method may further include flowing an intermediate product comprising the first amount of isobutane from the first catalyst bed to the heat exchanger. The method may further include cooling, by the heat exchanger, the intermediate product to form cooled intermediate product, and flowing the cooled intermediate product to the second catalyst bed. The method may further include isomerizing, in the second catalyst bed, at least some n-butane in the cooled intermediate product to form a second amount of isobutane. Further still, the method may include flowing a product stream comprising the first amount of isobutane and the second amount of isobutane from the second catalyst bed.

Embodiments of the invention include a method of isomerizing n-butane to form isobutane. The method may include heating a feed stream comprising n-butane to a temperature in a range of 120° C. to 190° C. by heat transfer with a heat exchange medium. The method may further include flowing the feed stream to a reactor. The reactor may comprise a first catalyst bed and a second catalyst bed. The first catalyst bed and the second catalyst bed may be separate so that catalyst in the first catalyst bed does not contact catalyst in the second catalyst bed. The reactor may further include a coiled heat exchanger disposed between the first catalyst bed and the second catalyst bed. The coiled heat exchanger is adapted to transfer heat via the heat exchange medium. The method may further comprise isomerizing, in the first catalyst bed, at least some of the n-butane in the feed stream to form a first amount of isobutane. The method may include flowing an intermediate product comprising the first amount of isobutane from the first catalyst bed to the coiled heat exchanger. The method may further include cooling, by the heat exchange medium in the coiled heat exchanger, the intermediate product. The method may further still include flowing the cooled intermediate product to the second catalyst bed and isomerizing, in the second catalyst bed, at least some n-butane, if any, in the cooled intermediate product to form a second amount of isobutane. The method may further still include flowing a product stream comprising the first amount of isobutane and the second amount of isobutane from the second catalyst bed. The conversion rate of n-butane to isobutane in the reactor is in a range of 32% to 67%.

Embodiments of the invention include a segmented reactor. The segmented reactor may include a first catalyst bed and a second catalyst bed. The first catalyst bed and the second catalyst bed may be separate so that catalyst in the first catalyst bed does not contact catalyst in the second catalyst bed. The segmented reactor may further include a first heat exchanger disposed between the first catalyst bed and the second catalyst bed. The segmented reactor may further include a reactor housing. The reactor housing may comprise a shell configured to enclose the first catalyst bed, the second catalyst bed and the first heat exchanger. The reactor housing may further include a reactor inlet for flowing a feed stream in the segmented reactor and a reactor outlet for flowing a product stream from the segmented reactor.

Embodiments of the invention include a segmented reactor system. The segmented reactor system may comprise a segmented reactor. The segmented reactor may include a first catalyst bed and a second catalyst bed. The first catalyst bed and the second catalyst bed may be separate so that catalyst in the first catalyst bed does not contact catalyst in the second catalyst bed. The segmented reactor may further include a first heat exchanger disposed between the first catalyst bed and the second catalyst bed. The segmented reactor may further include a reactor housing. The reactor housing may comprise a shell configured to enclose the first catalyst bed, the second catalyst bed, and the first heat exchanger. The reactor housing may further include a reactor inlet for flowing a feed stream in the segmented reactor and a reactor outlet for flowing a product stream from the segmented reactor. The segmented reactor system may further comprise a second heat exchanger in fluid communication with an inlet of the reactor. The second heat exchanger is configured to heat a feed stream before flowing the feed to the reactor.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective" as that term is used in the specification and/or claims, means adequate to accomplish a desired, expected, or intended result.

The term "$C_n$+ hydrocarbon" wherein n is a positive integer, e.g. 1, 2, 3, 4, or 5, as that term is used in the specification and/or claims, means any hydrocarbon having at least n number of carbon atom(s) per molecule.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention, at least twenty embodiments are now described. Embodiment 1 is a method of isomerizing n-butane to form isobutane. The method includes the steps of flowing a feed stream comprising n-butane to a reactor including a first catalyst bed and a second catalyst bed, wherein the first catalyst bed and the second catalyst bed are separate so that catalyst in the first catalyst bed does not contact catalyst in the second catalyst bed; and a heat exchanger disposed between the first catalyst bed and the second catalyst bed; isomerizing, in the first catalyst bed, at least some of the n-butane in the feed stream to form a first amount of isobutane; flowing an intermediate product containing the first amount of isobutane from the first catalyst bed to the heat exchanger; cooling, by the heat exchanger, the intermediate product to form cooled intermediate product; flowing the cooled intermediate product to the second catalyst bed; isomerizing, in the second catalyst bed, at least some n-butane, if any, in the cooled intermediate product to form a second amount of isobutane; and flowing a product stream containing the first amount of isobutane and the second amount of isobutane from the second catalyst bed. Embodiment 2 is the method of embodiment 1, further including the step of heating the feed stream containing n-butane with a heat exchange medium before flowing the feed stream to the reactor. Embodiment 3 is the method of embodiment 2, wherein the feed stream is heated to a temperature in a range of 120° C. to 190° C. Embodiment 4 is the method of any of embodiments 1 to 3, wherein the feed stream contains 0.1 to 100 wt. % n-butane, 0 to 4 wt. % isobutane, 0 to 10 wt. % of hydrogen, and 0 to 1 wt. % of $C_5$+ hydrocarbons. Embodiment 5 is the method of any of embodiments 1-4, wherein the first catalyst bed and the second catalyst bed are fixed beds. Embodiment 6 is the method of any of embodiments 1 to 5, wherein the heat exchanger in the reactor is a coiled heat exchanger. Embodiment 7 is the method of any of embodiments 1 to 6, wherein the heat exchanger includes a tubular-coiled steam heat exchange system. Embodiment 8 is the method of any of embodiments 1 to 7, wherein the cooling by the heat exchanger reduces the temperature of the intermediate product by between 15° C. and 45° C. Embodiment 9 is the method of any of embodiments 1 to 8, wherein the catalyst is selected from the group consisting of Zeolite Socony Mobil-5, platinum/$SO_4^{2-}$—$ZrO_2$, palladium/$SO_4^{2-}$—$ZrO_2$, $H_3PW_{12}O_{40}$, and combinations thereof. Embodiment 10 is the method of any of embodiments 1 to 9, wherein the isomerizing in the first catalyst bed and the isomerizing in the second catalyst bed are at a pressure in a range of 25 bar to 32 bar. Embodiment 11 is the method of any of embodiments 1 to 10, wherein the feed stream has a liquid hourly space velocity in a range of 0.5 $h^{-1}$ to 2.0 $h^{-1}$. Embodiment 12 is the method of any of embodiments 1 to 11, wherein a conversion rate of n-butane from the product stream is in a range of 32% to 67%.

Embodiment 13 is a segmented reactor system. The segmented reactor system includes a first catalyst bed and a second catalyst bed, wherein the first catalyst bed and the second catalyst bed are separate so that catalyst in the first catalyst bed does not contact catalyst in the second catalyst bed; a first heat exchanger disposed between the first catalyst bed and the second catalyst bed; and a reactor housing, the reactor housing including a shell configured to enclose the first catalyst bed, the second catalyst bed and the first heat exchanger; a reactor inlet for flowing a feed stream in the segmented reactor; and a reactor outlet for flowing a product stream from the segmented reactor. Embodiment 14 is the segmented reactor system of embodiment 13, further including a feed stream before flowing the feed stream to the reactor. Embodiment 15 is the segmented reactor system of embodiment 14 wherein the first heat exchanger includes a first medium inlet for heat exchange medium in fluid communication with a second medium outlet of the second heat exchanger; and a first medium outlet for heat exchange medium in fluid communication with a second inlet of the second heat exchanger. Embodiment 16 is the segmented reactor system of any of embodiments 13 to 15, further including a charge heater in fluid communication with the second heat exchanger and the reactor inlet of the reactor housing, wherein the charge heater is configured to heat the feed stream until the feed stream is substantially fully vaporized. Embodiment 17 is the segmented reactor system of any of embodiments 13 to 16, wherein the segmented reactor is an axial flow reactor. Embodiment 18 is the segmented reactor system of any of embodiments 13 to 17, wherein the first catalyst bed and the second catalyst bed are fixed beds. Embodiment 19 is the segmented reactor system of any of embodiments 13 to 18, wherein the first heat exchanger includes a coiled heat exchanger. Embodiment 20 is the segmented reactor system of embodiment 19, wherein the first heat exchanger includes a tubular-coiled steam heat exchange system.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for isomerizing n-butane to form isobutane. A segmented reactor comprising a first catalyst bed, a second catalyst bed, and a first heat exchanger is used for the isomerization reaction. In embodiments of the invention, a heat exchanger is disposed between the first catalyst bed and the second catalyst bed. By using this heat exchanger to extract heat from an intermediate product flowing from the first catalyst bed to the second catalyst bed, process control and process optimization can be improved, and the equipment costs can be reduced, compared to conventional methods that require the use of several heat exchange trains at the outlet of each of two serial reactors.

Figure 1:
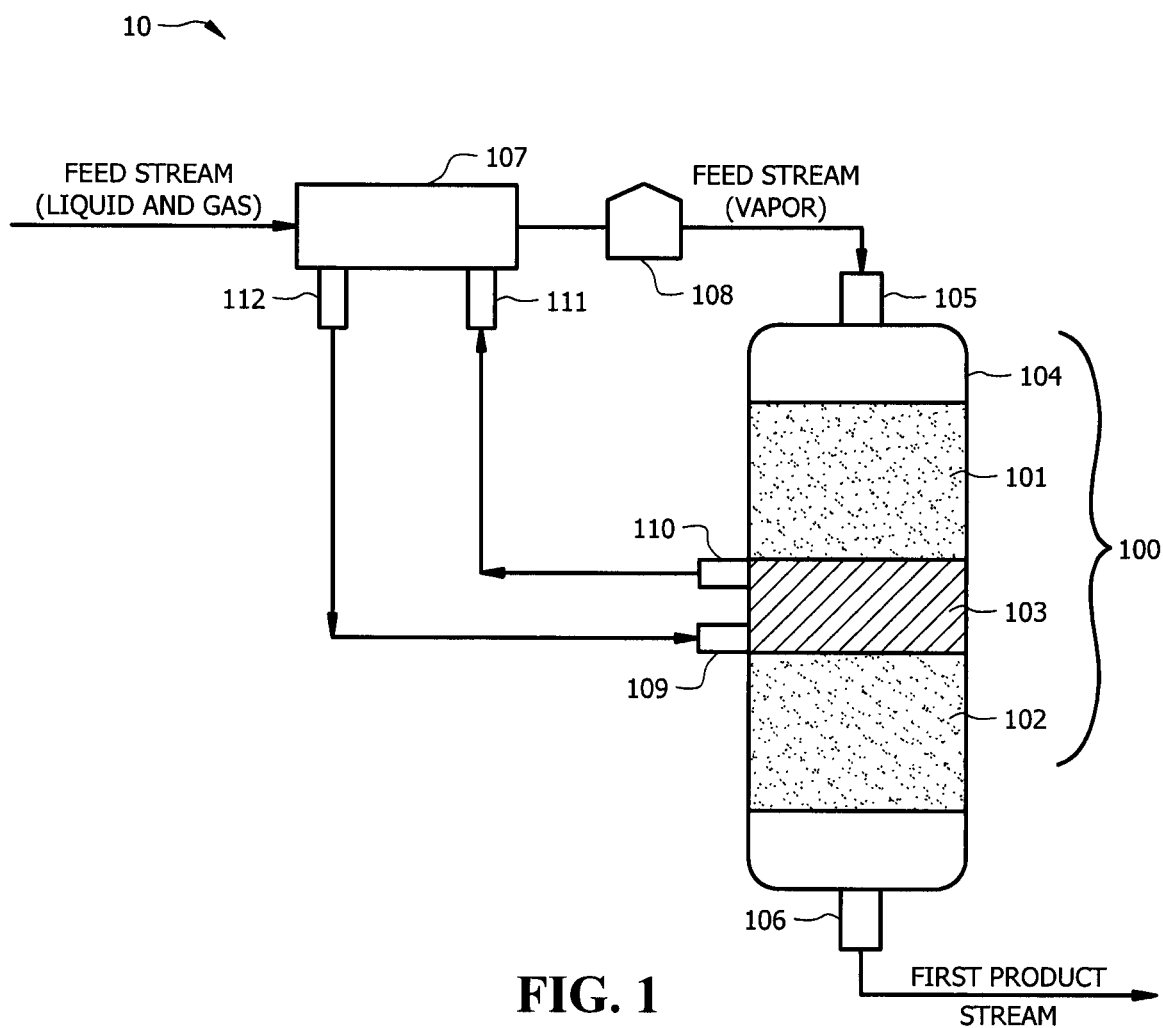
FIG. 1 shows a schematic diagram for a segmented reactor system, according to embodiments of the invention.

With reference to FIG. 1, a schematic diagram is shown of segmented reactor system 10. In embodiments of the invention, segmented reactor system 10 may be used for isomerizing n-butane to form isobutane. As shown in FIG. 1, segmented reactor system 10 may comprise segmented reactor 100. In embodiments of the invention, segmented reactor 100 may comprise first catalyst bed 101 and second catalyst bed 102. In embodiments of the invention, both first catalyst bed 101 and second catalyst bed 102 may be fixed beds. First catalyst bed 101 and second catalyst bed 102 may be separate such that catalyst in first catalyst bed 101 does not contact catalyst in second catalyst bed 102. The catalyst in first catalyst bed 101 and second catalyst bed 102 may include any isomerization catalyst that can catalyze isomerization of an alkane. In embodiments of the invention, exemplary catalysts may include, but are not limited to Zeolite Socony Mobil-5, platinum/$SO_4^{2-}$—$ZrO_2$, palladium/$SO_4^{2-}$—$ZrO_2$, $H_3PW_{12}O_{40}$, and combinations thereof.

In some conventional systems for isomerizing n-butane, two fixed bed reactors in series are used to react with n-butane. In embodiments of the invention, a total amount of catalyst in first catalyst bed 101 and second catalyst bed 102 may be less than or equal to the total amount of catalyst in the two fixed bed reactors in the conventional system for isomerizing n-butane to achieve substantially the same productivity of isobutane and n-butane conversion rate. In embodiments of the invention, segmented reactor 100 may further include first heat exchanger 103 disposed between first catalyst bed 101 and second catalyst bed 102. First heat exchanger 103 may be configured to extract heat from or provide heat to an intermediate product flowing from first catalyst bed 101 to second catalyst bed 102. Particularly, for isomerization of n-butane, first heat exchanger 103 may be used to extract heat from an intermediate product flowing from first catalyst bed 101 to second catalyst bed 102 because isomerization of n-butane to form isobutane is an exothermic process.

In embodiments of the invention, segmented reactor 100 may further comprise reactor housing 104. Reactor housing 104 may comprise a shell configured to enclose first catalyst bed 101, second catalyst bed 102, and first heat exchanger 103. Reactor housing 104 may further comprise reactor inlet 105 for flowing a feed stream in segmented reactor 100, and reactor outlet 106 for flowing a product stream from segmented reactor 100.

In embodiments of the invention, segmented reactor system 10 may further include second heat exchanger 107 in fluid communication with reactor inlet 105. Second heat exchanger 107 may be installed upstream of reactor inlet 105, configured to heat a feed stream before flowing the feed stream into segmented reactor 100. The catalytic process of the isomerization of n-butane occurs in vapor phase. Hence, according to embodiments of the invention, second heat exchanger 107 may heat the feed stream until it vaporizes. In embodiments of the invention, segmented reactor system 10 may further comprise charge heater 108 configured to heat feed stream until the feed is fully vaporized. Charge heater 108 may be installed after second heat exchanger 107 and before reactor inlet 105. Charge heater 108 may be used to heat the feed stream when at least part of the feed stream from heat exchanger 107 is not vaporized.

In embodiments of the invention, first heat exchanger 103 may comprise first medium inlet 109 for flowing exchange medium in first heat exchanger 103, and first medium outlet 110 for flowing exchange medium out from first heat exchanger 103. Second heat exchanger 107 may include second medium inlet 111 for flowing exchange medium in second heat exchanger 107, and second medium outlet 112 for flowing exchange medium out of second heat exchanger 107. In embodiments of the invention, first medium inlet 109 of first heat exchanger 103 is in fluid communication with second medium outlet 112 of second heat exchanger 107. Further, in embodiments of the invention, first medium outlet 110 of first heat exchanger 103 is in fluid communication with second medium inlet 111 of second heat exchanger 107. Thus, heat extracted from an intermediate product flowing from first catalyst bed 101 to second catalyst bed 102 by first heat exchanger 103 may be transferred to heat the feed stream via exchange medium flowing in second heat exchanger 107. In embodiments of the invention, first heat exchanger 103 may be a coiled heat exchanger or any other heat exchanger based on convective and conductive heat exchange mechanism. According to embodiments of the invention, first heat exchanger 103 may include a tubular-coiled steam heat exchange system.

According to embodiments of the invention, segmented reactor 100 may be an axial flow reactor. Although FIG. 1 shows segmented reactor 100 with two catalyst beds, in embodiments of the invention, segmented reactor 100 may comprise two or more catalyst beds. A heat exchanger may be disposed between each of two adjacent catalyst beds of a plurality of catalyst beds.

Figure 2:
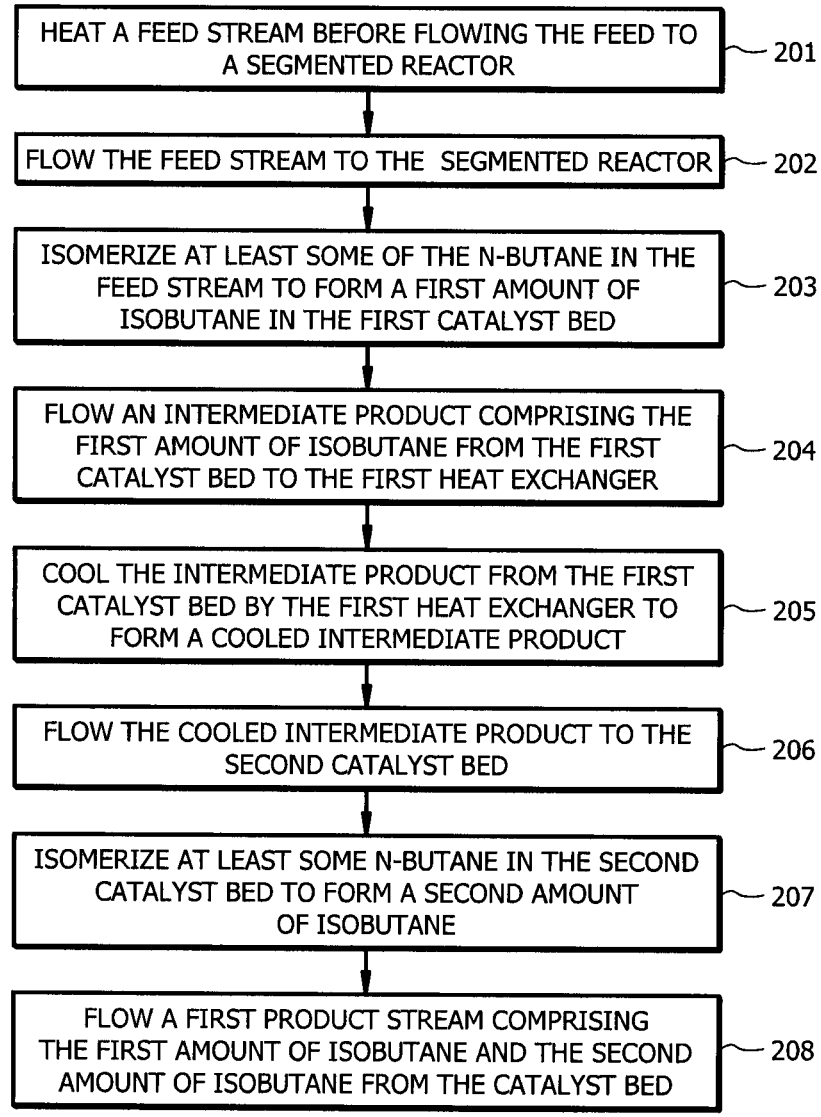
FIG. 2 shows a schematic flowchart for a method of isomerizing n-butane to form isobutane, according to embodiments of the invention.

FIG. 2 shows method 20 for isomerizing n-butane to form isobutane. Method 20 may be implemented by segmented reactor system 10 as shown in FIG. 1. According to embodiments of the invention, method 20 may start with heating a feed stream before flowing the feed stream to a reactor, as shown in block 201. The reactor may be segmented reactor 100. The feed stream may be heated by heat transfer carried out by second heat exchanger 107 and/or charge heater 108. In embodiments of the invention, charge heater 108 may heat the feed stream when the feed stream is not fully vaporized by second heat exchanger 107. In embodiments of the invention, the feed stream is heated to a temperature in a range of 120° C. to 190° C. and all ranges and values therebetween, including ranges of 120° C. to 125° C., 125° C. to 130° C., 130° C. to 135° C., 135° C. to 140° C., 140° C. to 145° C., 145° C. to 150° C., 150° C. to 155° C., 155° C. to 160° C., 160° C. to 165° C., 165° C. to 170° C., 170° C. to 175° C., 175° C. to 180° C., 180° C. to 185° C., or 185° C. to 190° C.

In embodiments of the invention, the feed stream may comprise n-butane at a concentration of 0.1 to 100 wt. %. According to embodiments of the invention, the feed stream may comprise primarily n-butane. The feed stream may further comprise isobutane at a concentration of 0 to 4 wt. % and all ranges and values therebetween, including ranges of 0 to 0.2 wt. %, 0.2 to 0.4 wt. %, 0.4 to 0.6 wt. %, 0.6 to 0.8 wt. %, 0.8 to 1.0 wt. %, 1.0 to 1.2 wt. %, 1.2 to 1.4 wt. %, 1.4 to 1.6 wt. %, 1.6 to 1.8 wt. %, 1.8 to 2.0 wt. %, 2.0 to 2.2 wt. %, 2.2 to 2.4 wt. %, 2.4 to 2.6 wt. %, 2.6 to 2.8 wt. %, 2.8 to 3.0 wt. %, 3.0 to 3.2 wt. %, 3.2 to 3.4 wt. %, 3.4 to 3.6 wt. %, 3.6 to 3.8 wt. %, or 3.8 to 4.0 wt. %. In embodiments of the invention, the feed stream may further include hydrogen at a concentration of 0 to 10 wt. % and all ranges and values therebetween, including 1 wt. %, 2 wt. %, 3 wt. %, 4 wt. %, 5 wt. %, 6 wt. %. 7 wt. %, 8 wt. %, 9 wt. %, or 10 wt. %. A small amount of $C_5+$ hydrocarbons may be included in the feed stream. A concentration of the $C_5+$ hydrocarbons may be in a range of 0 to 1 wt. % and all ranges and values therebetween, including 0 wt. %, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, or 1.0 wt. %.

Block 202 shows that the feed stream may be flowed to segmented reactor 100. The feed stream may be fully vaporized as shown in block 201 before entering segmented reactor 100. In embodiments of the invention, the feed stream has a liquid hourly space velocity (LHSV) in a range of 0.5 $h^{-1}$ to 2.0 $h^{-1}$ and all ranges and values therebetween, including ranges of 0.5 $h^{-1}$ to 0.6 $h^{-1}$, 0.6 $h^{-1}$ to 0.7 $h^{-1}$, 0.7 $h^{-1}$ to 0.8 $h^{-1}$, 0.8 $h^{-1}$ to 0.9 $h^{-1}$, 0.9 $h^{-1}$ to 1.0 $h^{-1}$, 1.0 $h^{-1}$ to 1.1 $h^{-1}$, 1.1 $h^{-1}$ to 1.2 $h^{-1}$, 1.2 $h^{-1}$ to 1.3 $h^{-1}$, 1.3 $h^{-1}$ to 1.4 $h^{-1}$, 1.4 $h^{-1}$ to 1.5 $h^{-1}$, 1.5 $h^{-1}$ to 1.6 $h^{-1}$, 1.6 $h^{-1}$ to 1.7 $h^{-1}$, 1.7 $h^{-1}$ to 1.8 $h^{-1}$, 1.8 $h^{-1}$ to 1.9 $h^-$, or 1.9 $h^{-1}$ to 2.0 $h^{-1}$.

As shown in block 203, method 20 may further include isomerizing, in first catalyst bed 101, at least some of the n-butane in the feed stream to form a first amount of isobutane. The isomerizing may be at a pressure in a range of 25 bar to 32 bar and all ranges and values therebetween including ranges of 25 bar to 26 bar, 26 bar to 27 bar, 27 bar to 28 bar, 28 bar to 29 bar, 29 bar to 30 bar, 30 bar to 31 bar, or 31 bar to 32 bar. As described above, according to embodiments of the invention, first catalyst bed 101 may be any isomerizing catalyst that can catalyze isomerization of an alkane. Exemplary catalysts may include, but are not limited to Zeolite Socony Mobil-5, platinum//$SO_4^{2-}$—$ZrO_2$, palladium/$SO_4^{2-}$—$ZrO_2$, $H_3PW_{12}O_{40}$, and combinations thereof. A conversion rate of n-butane from first catalyst bed 101 may be in a range of 1 to 67% and all ranges and values therebetween, including ranges of 1 to 5%, 5 to 10%, 10 to 15%, 15 to 20%, 20 to 25%, 25 to 30%, 30 to 35%, 25 to 40%, 40 to 45%, 45 to 50%, 50 to 55%, 55 to 60%, and 60 to 67%.

As shown in block 204, method 20 may further include flowing an intermediate product comprising the first amount of isobutane from first catalyst bed 101 to first heat exchanger 103. According to embodiments of the invention, the intermediate product may comprise 1 to 65 wt. % isobutane, 35 to 99 wt. % n-butane, 0.0002 to 0.5 wt. % hydrogen and 0.001 to 20 wt. % $C_5+$ compounds. In embodiments of the invention, the intermediate product from first catalyst bed 101 may be at a temperature of 110 to 250° C. and all ranges and values therebetween including ranges of 110 to 120° C., 120 to 130° C., 130 to 140° C., 140 to 150° C., 150 to 160° C., 160 to 170° C., 170 to 180° C., 180 to 190° C., 190 to 200° C., 200 to 210° C., 210 to 220° C., 220 to 230° C., 230 to 240° C., and 240 to 250° C. Block 205 shows that the first intermediate product from first catalyst bed 101 may be cooled by first heat exchanger 103 to form a cooled intermediate product. In embodiments of the invention, cooling by first heat exchanger 103 may reduce the temperature of the intermediate product by between 15° C. to 45° C., and all ranges and values therebetween, including 15° C. to 18° C., 18° C. to 21° C., 21° C. to 24° C., 24° C. to 27° C., 27° C. to 30° C., 30° C. to 33° C., 33° C. to 36° C., 36° C. to 39° C., 39° C. to 42° C., or 42° C. to 45° C.

Block 206 shows that method 20 may further include flowing the cooled intermediate product to second catalyst bed 102. As shown in block 207, at least some n-butane, if any, may be isomerized in second catalyst bed 102 to form a second amount of isobutane. Second catalyst bed may comprise any isomerization catalyst for alkane isomerization. Exemplary catalysts may include, but are not limited to Zeolite Socony Mobil-5, platinum/$SO_4^{2-}$—$ZrO_2$, palladium/$SO_4^{2-}$—$ZrO_2$, $H_3PW_{12}O_{40}$, and combinations thereof. Similar to isomerization in first catalyst bed 101, a reaction pressure in second catalyst bed may be in a range of 25 bar to 32 bar and all ranges and values therebetween.

As shown in block 208, a first product stream comprising the first amount of isobutane and the second amount of isobutane may be flowed from second catalyst bed 102. In embodiments of the invention, a final conversion rate of n-butane in the first product stream from second catalyst bed 102 may be in a range of 32% to 67% and all ranges and values therebetween, including ranges of 32% to 35%, 35% to 38%, 38% to 41%, 41% to 44%, 44% to 47%, 47% to 50%, 50% to 53%, 53% to 56%, 56% to 59%, 59% to 62%, 62% to 65%, or 65% to 67%. In embodiments of the invention, the first product stream from second catalyst bed 102 may be at a temperature of 100 to 250° C. and all ranges and values therebetween, including ranges of 100 to 110° C., 110 to 120° C., 120 to 130° C., 130 to 140° C., 140 to 150° C., 150 to 160° C., 160 to 170° C., 170 to 180° C., 180 to 190° C., 190 to 200° C., 200 to 210° C., 210 to 220° C., 220 to 230° C., 230 to 240° C., and 240 to 250° C. The isobutane from the first product stream may be used to produce methyl-tertiary-butyl-ether.

In summary, embodiments of the invention involve systems and methods for isomerizing n-butane to form isobutane. The methods may include using systems that comprise a segmented reactor including a first catalyst bed and a second catalyst bed. The first catalyst bed and the second catalyst bed may be separated by a first heat exchanger configured to extract heat from an intermediate product flowing from the first catalyst bed to the second catalyst bed. By using the system, the operating process and the process control can both be simplified compared to a conventional system that comprises two separated reactors in series and several heat exchange trains for each of the reactors. Therefore, the systems and the methods of using the system to isomerize n-butane, according to embodiments of the invention, may reduce the costs for equipment, operating, and process control.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of isomerizing n-butane to form isobutane, the method comprising:
   flowing a feed stream comprising n-butane to a reactor, the reactor comprising:
   a first catalyst bed and a second catalyst bed, wherein the first catalyst bed and the second catalyst bed are separate so that catalyst in the first catalyst bed does not contact catalyst in the second catalyst bed; and
   a heat exchanger disposed between the first catalyst bed and the second catalyst bed;
   isomerizing, in the first catalyst bed, at least some of the n-butane in the feed stream to form a first amount of isobutane;
   flowing an intermediate product comprising the first amount of isobutane from the first catalyst bed to the heat exchanger;
   cooling, by the heat exchanger, the intermediate product to form cooled intermediate product;
   flowing the cooled intermediate product to the second catalyst bed;
   isomerizing, in the second catalyst bed, at least some n-butane, if any, in the cooled intermediate product to form a second amount of isobutane; and
   flowing a product stream comprising the first amount of isobutane and the second amount of isobutane from the second catalyst bed;
   wherein the first catalyst bed comprises an isomerizing catalyst that can catalyze isomerization of n-butane.

2. The method of claim 1, further comprising:
   heating the feed stream comprising n-butane with a heat exchange medium before flowing the feed stream to the reactor.

3. The method of claim 2, wherein the feed stream is heated to a temperature in a range of 120° C. to 190° C.

4. The method of claim 1, wherein the feed stream comprises 0.1 to 100 wt. % n-butane, 0 to 4 wt. % isobutane, 0 to 10 wt. % of hydrogen, and 0 to 1 wt. % of $C_{5+}$ hydrocarbons.

5. The method of claim 1, wherein the first catalyst bed and the second catalyst bed are fixed beds.

6. The method of claim 1, wherein the heat exchanger in the reactor is a coiled heat exchanger.

7. The method of claim 1, wherein the heat exchanger comprises a tubular-coiled steam heat exchange system.

8. The method of claim 1, wherein the cooling by the heat exchanger reduces the temperature of the intermediate product by between 15° C. and 45° C.

9. The method of claim 1, wherein the isomerizing catalyst is selected from the group consisting of Zeolite Socony Mobil-5, platinum/$SO_4^{2-}$—$ZrO_2$, palladium/$SO_4^{2-}$—$ZrO_2$, $H_3PW_{12}O_{40}$, and combinations thereof.

10. The method of claim 1, wherein the isomerizing in the first catalyst bed and the isomerizing in the second catalyst bed are at a pressure in a range of 25 bar to 32 bar.

11. The method of claim 1, wherein the feed stream has a liquid hourly space velocity in a range of 0.5 $h^{-1}$ to 2.0 $h^{-1}$.

12. The method of claim 1, wherein a conversion rate of n-butane from the product stream is in a range of 32% to 67%.

13. A segmented reactor system comprising:
   a segmented reactor comprising:
   a first catalyst bed and a second catalyst bed, wherein the first catalyst bed and the second catalyst bed are separate so that catalyst in the first catalyst bed does not contact catalyst in the second catalyst bed;
   a first heat exchanger disposed between the first catalyst bed and the second catalyst bed; and
   a reactor housing comprising:
   a shell configured to enclose the first catalyst bed, the second catalyst bed and the first heat exchanger;
   a reactor inlet for flowing a feed stream in the segmented reactor;
   a reactor outlet for flowing a product stream from the segmented reactor;
   wherein the first catalyst bed comprises an isomerizing catalyst that can catalyze isomerization of n-butane;
   a second heat exchanger in fluid communication with the reactor inlet, configured to heat a feed stream before flowing the feed stream to the reactor; and a charge heater in fluid communication with a second heat exchanger and the reactor inlet of the reactor housing, wherein the charge heater is configured to heat the feed stream until the feed stream is substantially fully vaporized.

14. The segmented reactor system of claim 13, wherein the first heat exchanger comprises:
a first medium inlet for heat exchange medium in fluid communication with a second medium outlet of the second heat exchanger; and a first medium outlet for heat exchange medium in fluid communication with a second inlet of the second heat exchanger.

15. The segmented reactor system of claim 13, wherein the segmented reactor is an axial flow reactor.

16. The segmented reactor system of claim 13, wherein the first catalyst bed and the second catalyst bed are fixed beds.

17. The segmented reactor system of claim 13, wherein the first heat exchanger comprises a coiled heat exchanger.

18. The segmented reactor system of claim 17, wherein the first heat exchanger includes a tubular-coiled steam heat exchange system.

\* \* \* \* \*